United States Patent [19]
DeSatnick

[11] Patent Number: 5,571,184
[45] Date of Patent: Nov. 5, 1996

[54] GRAFT FIXATION DEVICE AND METHOD OF USING

[75] Inventor: Allen DeSatnick, Marblehead, Mass.

[73] Assignee: Wright Medical Technology, Inc., Arlington, Tenn.

[21] Appl. No.: 482,472

[22] Filed: Jun. 7, 1995

[51] Int. Cl.$^6$ .................................................. A61F 2/08
[52] U.S. Cl. .................... 623/13; 623/16; 606/72; 606/73; 606/151; 403/368; 403/370; 403/371
[58] Field of Search .................... 623/11, 13, 14, 623/16; 606/60, 65, 72, 73, 151; 411/267, 270, 433; 403/368, 370, 371

[56] References Cited

U.S. PATENT DOCUMENTS

| | | | |
|---|---|---|---|
| 1,120,410 | 12/1914 | Rohmer et al. | 403/370 |
| 1,717,665 | 6/1929 | Conner | 403/368 |
| 3,361,460 | 1/1968 | Jansen | 403/370 |
| 3,514,137 | 5/1970 | Brown et al. | 403/371 |
| 3,717,367 | 2/1973 | Peter et al. | 403/371 |
| 4,537,185 | 8/1985 | Stednitz . | |
| 4,828,562 | 5/1989 | Kenna | 623/13 |
| 5,067,956 | 11/1991 | Buford, III et al. . | |
| 5,151,104 | 9/1992 | Kenna | 623/13 |
| 5,152,790 | 10/1992 | Rosenberg et al. | 623/13 |
| 5,356,413 | 10/1994 | Martins et al. . | |
| 5,403,136 | 4/1995 | Mathys | 606/73 |
| 5,425,766 | 6/1995 | Bowald | 623/13 |
| 5,425,767 | 6/1995 | Steininger et al. . | |
| 5,458,601 | 10/1995 | Young, Jr. et al. | 606/73 |

FOREIGN PATENT DOCUMENTS

| | | | |
|---|---|---|---|
| 0413549 | 2/1991 | European Pat. Off. | 623/13 |
| 0593795 | 8/1925 | France | 411/267 |
| 3630390 | 3/1987 | Germany | 606/72 |

Primary Examiner—John G. Weiss
Assistant Examiner—Francis K. Cuddihy
Attorney, Agent, or Firm—Lappin & Kusmer LLP

[57] ABSTRACT

A graft fixation device and methods for using them. The device comprises a collar disposed about a central axis and having a threaded interior surface, an optionally threaded exterior surface, first and second annular drive elements disposed concentrically within the collar and externally threaded for engagement with the collar, and a graft securing element disposed concentrically between the drive elements. The collar and first drive element include driver elements at their respective, first ends for receiving a rotatable driver. The first drive element is rotatable relative to the collar for axial advancement toward the second drive element such that the graft securing element is sandwiched between the drive elements to form a unitary structure. The collar is rotatable relative to the unitary structure of the drive elements and graft securing element for moving the graft axially to apply a desired axial tension thereto. The unitary structure is also rotatable relative to the collar for applying a spiral twist to the graft.

9 Claims, 7 Drawing Sheets

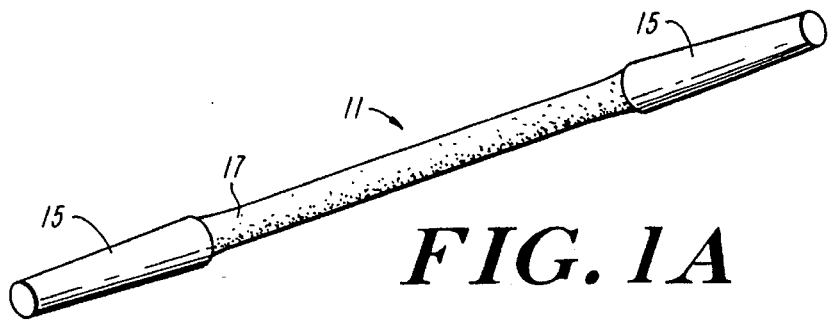
FIG. 1A
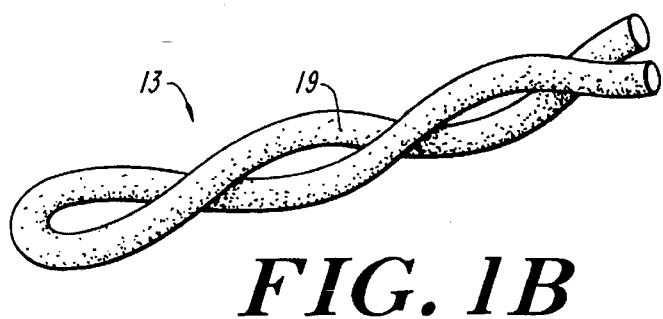
FIG. 1B
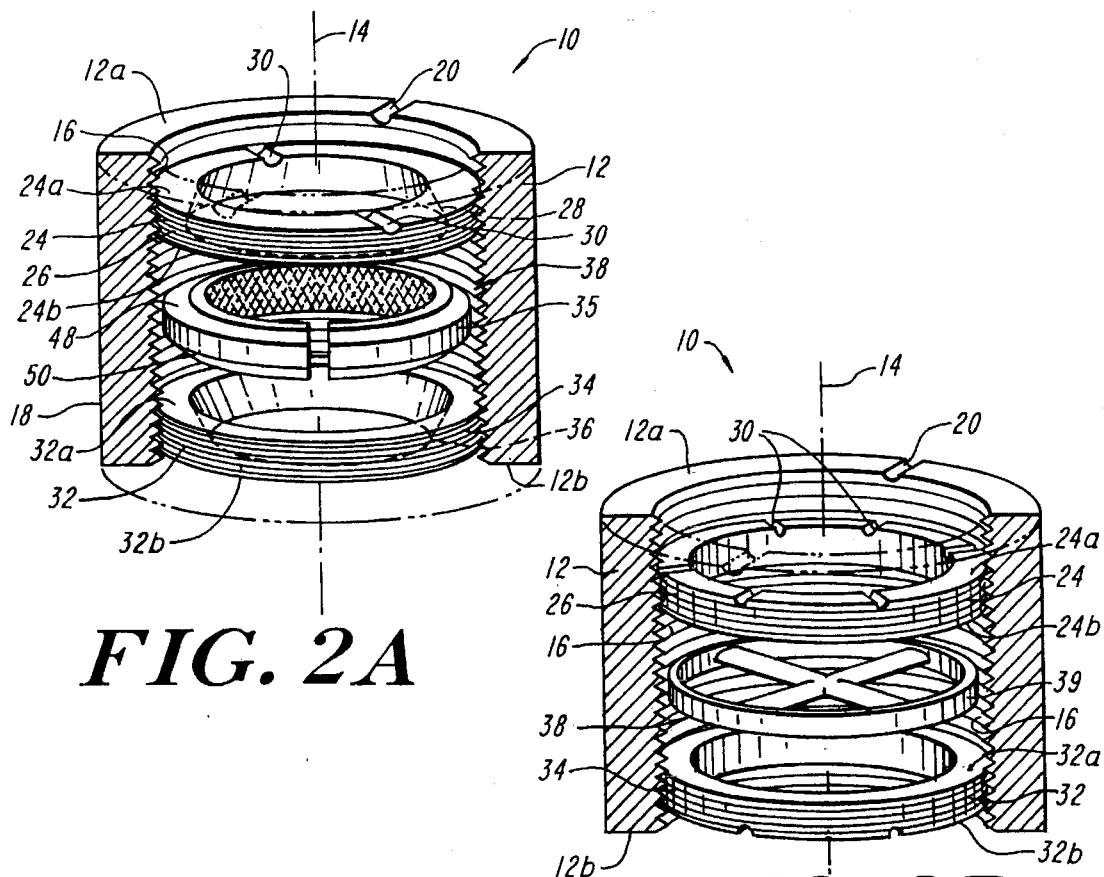
FIG. 2A
FIG. 2B

GRAFT FIXATION DEVICE AND METHOD OF USING

TECHNICAL FIELD

This invention relates to fastening devices for use in bony tissue. More particularly, the invention relates to fastening devices for tensioning and fixing a bony portion of a ligament substitute, such as a graft, in a patient.

BACKGROUND OF THE INVENTION

Ligaments are elongated bands of collagenous connective tissue which interconnect bones and stabilize the movement of bones relative to one another. Each end of a ligament is affixed to a bone. Torn ligaments, particularly in the knee, ankle and shoulder, are common injuries among athletes and frequently require extensive reconstruction or replacement.

Unlike vascular tissue, such as bone and skin, torn or damaged ligaments do not naturally heal because they are not vascularized, i.e., they are not supplied with a network of blood vessels which provide blood and lymph for tissue regeneration and repair. Thus, they must either be repaired, if possible, or replaced with a substitute material which will simulate the biomechanical properties of the original ligament. Surgical repair of a torn ligament, such as by mending, does not restore full strength and elasticity to the ligament and is thus of limited benefit. On the other hand, surgical replacement of a torn or damaged ligament with a natural or artificial prosthesis can substantially restore normal patient activity levels and is frequently prescribed. However, in the case of replacement with a natural or synthetic substitute, the replacement ligament must be affixed to the respective bones in a manner permitting substantially similar function to the original ligament.

The anterior cruciate ligament (ACL) connects the femur and the tibia within a knee joint. The ACL is the single most important stabilizing structure within the knee: it limits the movement of the bones of the joint and resists anterior displacement of the tibia with respect to the femur at all flexion positions. The ACL also resists forces which tend to hyperextend the knee.

Ruptures of the anterior cruciate ligament are among the most common injury to the knee. It is estimated that half a million ACL reconstructions are performed per year in the United States alone, with that number doubling for ACL reconstructions worldwide. Reconstruction of the ACL is a highly demanding procedure involving a determination of the correct anatomic location for an ACL substitute, the location and preparation of bony tunnel sites for the ACL substitute, and proper in situ fixation and tensioning of the ACL substitute.

One of the most widely used ACL substitutes is the bone-patellar tendon-bone (BPTB) graft. The term "graft", as used herein, refers to a natural or synthetic implantable substitute for various kinds of tissue. The central one-third of the patient's or a donor's patellar tendon, along with portions of the bony insertions of the patellar tendon, are used as a replacement for the damaged ACL. The bony insertions are preferably harvested as cylindrical bone plugs to facilitate implantation and fixation of the BPTB graft into osseous tunnels of the patient's knee joint. The BPTB graft is a popular choice for ACL reconstructive surgery because of its high load strength and its superior bone fixation properties.

Another commonly used ACL substitute is the iliotibial band (ITB) graft. The ITB is a section of ligament which can be harvested from a portion of a patient's or a donor's iliotibial ligament located within the anterolateral ligament structures of the knee joint.

Generally, to use such BPTB or ITB grafts, an osseous tunnel is established in both the femur and tibia of a patient, and the bone plugs of the BPTB graft, or the ends of the ITB graft, are positioned within, and affixed to, the tunnels, with a predetermined tension and angular orientation established in the tendon. In order to promote effective fusion of the bone plugs of a BPTB graft to the side walls of the osseous channels, a close fit, and preferably direct contact, is desired. It is also important, from a functional standpoint, to have a specific tension in the ligament when it is anchored in place.

Identification of the optimal location and tension of such a graft and, once identified, accomplishing the identified location and tension, are difficult tasks. Generally, the surgeon lacks adequate equipment for precisely determining the appropriate anatomic location for correct placement of the graft, for preparing the bony tunnel sites, and for anchoring and tensioning the graft, and often a limited trial-and-error approach is used.

Various devices for fixing ligaments and ligament substitutes to bone are known. For example, U.S. Pat. No. 4,537,185 to Stednitz discloses a self-drilling, self-tapping cannulated fixation screw which can be inserted over a guide wire and positioned in a desired location within a bone. Such bone screws are commonly used as graft fixation devices for the bone plugs of BPTB grafts. In such cases, a bone screw is inserted into the interfacial space between the bone plug at the graft and the wall of the osseous tunnel to establish an interference fit. Although this approach may effectively secure the bone plug in the channel ligament, the screw necessarily creates a gap on one side of the plug while driving the other side of the bone plug against the sidewall of the tunnel. This less-than-360 degree contact is less than optimal.

Other fixation devices employ various structures for coupling with a ligament or a suture and for engaging with the bone. For example, U.S. Pat. No. 5,356,435 to Thein discloses an element for fixing a ligament in a bony canal. The element includes an internal conduit for receiving an end of a ligament, and a clamping structure for securing the ligament end within the conduit. U.S. Pat. No. 5,356,413 to Martins et al. discloses a surgical anchor having a body portion and a suture-receiving bore. The body portion includes a rearward portion adapted for receiving a ligament, and a plurality of barbs extending outwardly and rearwardly from the body for engaging with the walls of a bony tunnel in a force fit.

None of these fixation devices permits a surgeon to easily fix the fibrous or bony portions of a ligament substitute in a desired position within a bony tunnel (e.g., in full 360-degree contact with the channel walls) and also establish the desired tension and angular orientation in the ligament substitute in situ. The grafted ligament substitute which is fixed with these devices may loosen under load as a result of the asymmetric positioning of the fixation device in the bony tunnel with respect to the graft and the forces on the joint. Also, torque applied to a bone screw to fix a graft may be undesirably transferred to the graft itself, thereby changing the orientation of the ligament substitute in the bony tunnel. Also, if removal of the bone screw is required, it must be either unscrewed or chipped out, leaving an untilled hole in the bone. Also, some fixation devices are relatively large in cross-section, requiring a bony canal of relatively large diameter. Damaged or diseased host tissue may not be sufficiently strong or extensive to permit the use of large fixation devices therein.

It is therefore an object of the present invention to provide a graft fixation device which obviates the disadvantages of the prior art devices.

It is another object of the present invention to provide a graft fixation device which can establish in situ a desired tension in a ligament graft.

It is another object of the present invention to provide a graft fixation device which can establish in situ a desired axial position for a ligament graft.

Yet another object of the present invention to provide a graft fixation device which can also be used to rotate a ligament graft in situ about its longitudinal axis to achieve a desired angular orientation or create a desired spiral twist in the graft.

It is another object of the present invention to provide a graft fixation device which is minimally invasive to a patient.

SUMMARY OF THE INVENTION

These and other objects of the invention are achieved by the present invention which, in one aspect, provides a graft fixation device. In one form, the device comprises an annular collar disposed about and extending along a central axis. The collar has a first end, a second end, an interior lateral surface, and an exterior lateral surface. The interior lateral surface is threaded about and along the central axis. The collar has at its first end a collar driver element for receiving an external driver rotatable about the central axis.

The device includes a first annular drive element disposed concentrically within the collar and having a first end closest to the first end of the collar and a second end opposite the first end. The first annular drive element has an outer lateral surface in threaded engagement with the threaded interior surface of the collar.

The device further includes a second annular drive element disposed concentrically within the collar and having a first end closest to the second end of the collar and a second end opposite the first end. The second annular drive element has an outer lateral surface in threaded engagement with the threaded interior surface of the collar. The device also has a first driver element at the first end of the drive element for receiving an external driver rotatable about the central axis.

The device is further adapted to releasably secure at least a portion of the graft concentrically within the collar between the first and second drive elements.

In one form, the first annular drive element has a conical inner lateral surface disposed about the central axis with a relatively small radius near the first end of the drive element and a relatively large radius near the second end of the drive element. The second annular drive element also has a conical inner lateral surface disposed about the central axis. The conical inner lateral surface has a relatively small radius near the first end of the drive element and a relatively large radius near the second end of the drive element. In this embodiment, the graft securing element comprises a radially compressible split collet. The collet extends circumferentially between two circumferential ends separated by a gap and has a first axial end closest to the first drive element, a second axial end closest to the second drive element, an interior surface adapted for frictional engagement with an object interior thereto, and an outer lateral surface having a first tapered conical portion near the first axial end of the collet and a second tapered conical portion near the second axial end of the collet.

The interior surface of the collet is adapted to prevent axial movement of the graft along the central axis. By way of example, that surface may include a plurality of circumferentially extending ridges. The ridges can have a sawtooth or helical tooth profile extending toward the central axis. In a preferred embodiment, the ridges have an asymmetrical profile with the ridge surfaces closest to the first end of the drive element being transverse to the central axis.

This configuration permits the device to be positioned within a bony tunnel and allows the bone plug of a graft to be affixed to the device in situ in a manner permitting in situ adjustment of tension, angular orientation and axial position of the bone plug.

In another embodiment, the exterior lateral surface of the collar is also threaded about and along the central axis.

In still another embodiment, the graft securing element comprises a disk fastener having a plurality of apertures for receiving at least a portion of a graft segment.

According to another aspect of the invention, there is provided a method for in situ anchoring of a graft to an interior wall of a bone channel extending along a channel axis, while permitting in situ adjustment of the axial position and angular orientation and tension of the graft. A graft fixation device as previously described, preferably with the first drive element axially separated from said second drive element, is provided. The fixation device is positioned within the channel so that the central axis and the channel axis are substantially colinear and the collar is fixedly positioned with respect to the channel wall. A segment of the graft is positioned within the graft securing element, and a rotatable driver is applied to the first driver element to rotate the first drive element relative to the collar. The first drive element axially advances toward the second drive element to engage the graft securing element between them so that the graft segment is axially fixed with respect to the drive elements.

Once the graft securing element is fixed between the first and second drive elements, further rotation of the first drive element with the rotatable driver rotates the drive elements and graft securing element therebetween as a unitary structure, thereby imparting a twist to the tendon secured thereby.

A rotatable driver can also be used to rotate the collar relative to the unitary structure of the drive elements and the graft securing element in order to apply axial tension to the graft in situ.

According to another aspect of the invention, there is provided a method for anchoring a bone plug of a BPTB graft to an interior wall of a bony tunnel which extends along a channel axis. The method comprises the steps of providing a graft fixation device generally of the type described above. According to the method, the first drive element is initially axially separated from the second drive element so that the gap of the collet is relatively large. The fixation device is positioned within the bony tunnel so that the central axis and the channel axis are substantially colinear and the exterior surface of the fixation device is fixedly positioned with respect to the channel wall. A bone plug, from a BPTB graft, is positioned within the interior of the collet, and a rotatable driver is applied to the first driver element to rotate the first drive element relative to the collar. This rotation of the first drive element axially advances it toward the second drive element so that the conical surfaces of the first and second drive elements engage the tapered conical portions of the outer lateral surface of the collet and radially compress the collet so that the gap is relatively small. As the gap decreases, the effective diameter of the collet decreases. The interior lateral surface of the collet frictionally engages the bone plug to fix it axially with respect to the collar.

The method can further include the step of applying a rotatable driver to the collar driver element to rotate the collar relative to the unitary structure of the drive elements and collet to apply axial tension on the graft in situ.

The method can further include the step of applying a rotatable driver to the driver element on the first drive element to rotate the drive elements and collet as a unit relative to the collar to impart a helical or spiral twist to the graft in situ.

According to another aspect of the invention, there is provided a method for anchoring a graft to an interior wall of a bone channel drilled from a single entry portal in the tibia and having various different channel diameters.

These and other features of the invention will be more fully appreciated with reference to the following detailed description which is to be read in conjunction with the attached drawings.

BRIEF DESCRIPTION OF THE DRAWINGS

The invention is further described by the following description and Figures, in which:

FIG. 1A is a perspective view of a BPTB graft;

FIG. 1B is a perspective view of an ITB graft;

FIG. 2A is a partial cutaway view of a graft fixation device according to one embodiment of the present invention;

FIG. 2B is a partial cutaway view of a graft fixation device according to another embodiment of the invention;

DESCRIPTION OF THE PREFERRED EMBODIMENTS

Figure 3A:
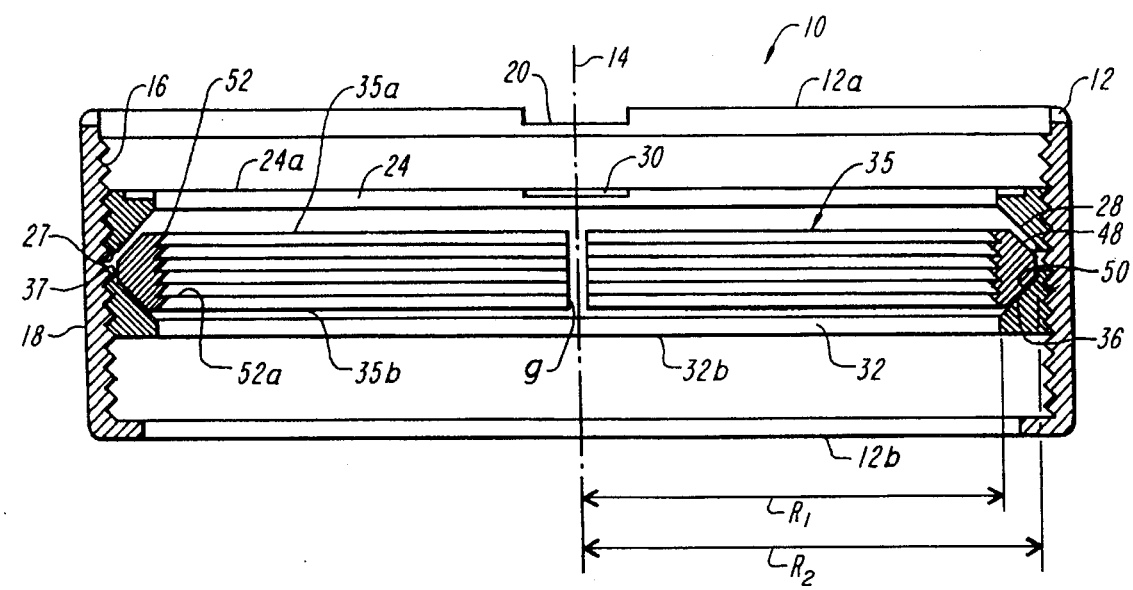
FIG. 3A is a lateral cross-sectional view of the graft fixation device of FIG. 2A in which the drive elements are axially spaced apart from the graft securing element.

The graft fixation device of the present invention can be used to fix either a fibrous or a bony segment of a graft, such as a BPTB or ITB ligament substitute, within a bony tunnel or channel. It can also be used to apply a desired axial tension and/or spiral twist to the graft once the graft is fixed in place in the bony channel.

FIGS. 1A and 1B illustrate, respectively, a BPTB graft 11 and an ITB graft 13. The BPTB graft of FIG. 1A is harvested from the central third of the patient's or a donor's patellar tendon and comprises bone plugs 15 at each end of a section of patellar tendon 17. The bone plugs are preferably cylindrical to promote ease of graft insertion in the bony channel. The ITB graft of FIG. 1B is harvested from the patient's or a donor's iliotibial ligament band in the knee joint and comprises one or more lengths of ligament 19 which can be looped, twisted or braided to enhance its strength as a graft.

As shown in FIGS. 2A and 2B, the graft fixation device 10 of the present invention comprises a collar 12 in the shape of an annulus. The collar 12 is disposed about a central axis 14. Disposed concentrically within the collar 12 are first and second annular drive elements 24, 32 and a graft securing element 38. The collar 12 and the first drive element 24 include, respectively, collar driver element 20 and first driver element 30 for receiving a rotatable driver 22 (shown in FIGS. 5–6).

The collar 12 has first and second opposing ends 12a, 12b. Collar driver element 20 at the first end 12a, shown as a slot in FIGS. 2A, 2B, 3A and 3B, is adapted to receive a rotatable driver 22 which can be rotated about the central axis 14.

The collar 12 has an interior lateral surface 16 which is threaded, and an exterior lateral surface 18 which can be smooth, knurled, threaded or otherwise finished to promote tissue induction. In one preferred embodiment of the invention, discussed in greater detail below, the exterior lateral surface 18 of the collar 12 is threaded.

The first annular drive element 24 is disposed concentrically within the collar 12 near the first end 12a of the collar. The first drive element 24 has a first end 24a near the first end 12a of the collar, and a second end 24b near the second end 12b of the collar. The first drive element 24 also has an outer lateral surface 26 which is threaded for threaded engagement with the interior lateral surface 16 of the collar. The first drive element 24 further includes a first driver element 30, shown as a slot in FIGS. 2A, 2B, 3A and 3B, in its first end 24a for receiving a rotatable driver 22.

The second annular drive element 32 is also disposed concentrically within the collar 12. The second drive element 32 has a first end 32a which is nearest the second end 24b of the first drive element 24, and a second end 32b which is nearest the second end 12b of the collar 12. The second drive element 32 also has an outer lateral surface 34 which is threaded for threaded engagement with the interior lateral surface 16 of the collar 12.

Figure 3B:
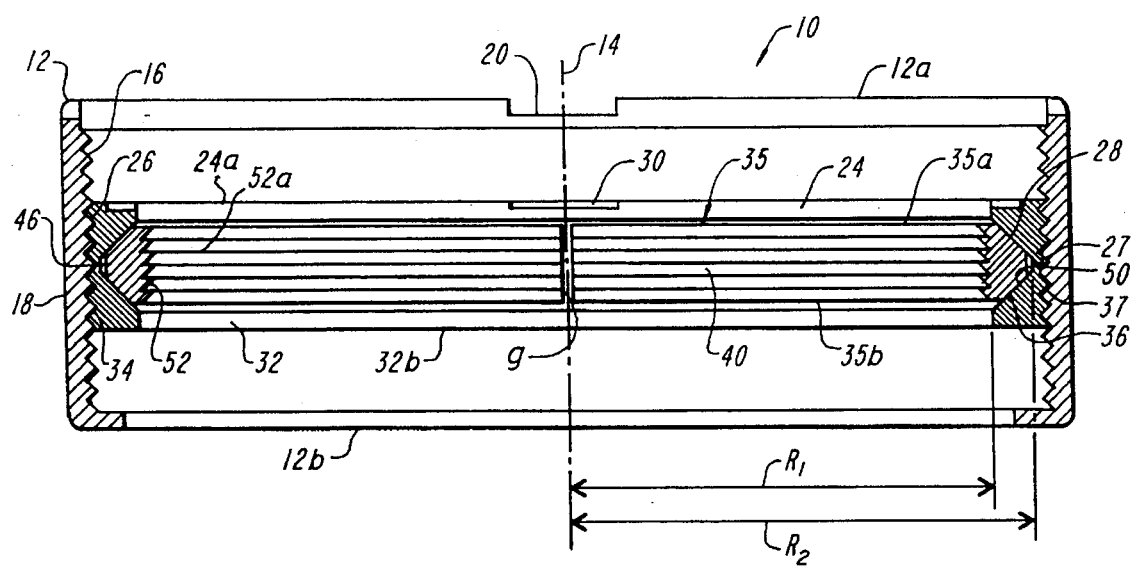
FIG. 3B is a lateral cross-sectional view of the graft fixation device of FIG. 2A in which the drive elements are engaged around the graft securing element to form a unitary structure.

In one embodiment, as shown in FIGS. 2A, 3A and 3B, the first drive element 24 includes a conical lateral inner surface 28 which is disposed about the central axis 14. The conical inner surface 28 has a relatively small radius $R_1$ near the first end 24a of the drive element 24 and a relatively large radius $R_2$ near the second end 24b of the drive element. The second drive element 32 also has a conical lateral inner surface 36 which is disposed about the central axis 14. The conical inner surface 36 has a relatively large radius $R_2$ near the first end 32a of the second driver element 32 and a relatively small radius $R_1$ near the second end 32b of the driver.

Figure 4A:
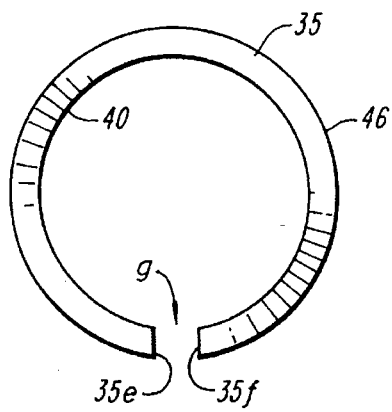
FIG. 4A is a plan view of a graft securing element according to one embodiment of the invention.
Figure 4C:
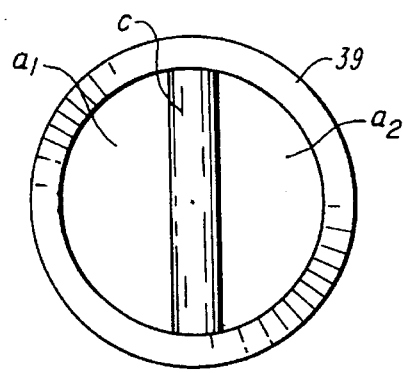
FIG. 4C is a plan view of a graft securing element according to another embodiment of the invention.
Figure 4B:
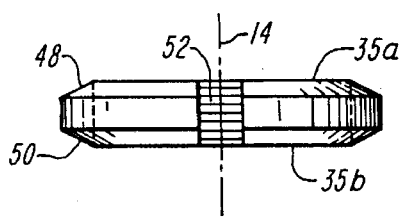
FIG. 4B is a side elevational view of the graft securing element of FIG. 4A.
Figure 4D:
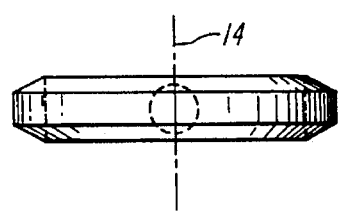
FIG. 4D is a side elevational view of the graft securing element of FIG. 4C.

In the embodiment shown in FIGS. 2A, 3A and 3B, the graft securing element 38 comprises a radially compressible split collet 35 which is concentrically disposed within the collar 12 between the first and second drive elements 24, 32. As shown in greater detail in FIGS. 4A and 4B, the collet 35 has a first axial end 35a closest to the first drive element 24 and a second axial end 35b closest to the second drive element 32. The collet 35 extends and compresses circumferentially about the central axis 14 by means of a variable-width gap g between two circumferential ends 35e, 35f. It has an interior surface 40 which is adapted for frictional engagement with an object, such as a bony segment 42 of a bone graft 44. It also has an outer lateral surface 46 with a first tapered conical portion 48 near the first axial end 35a of the collet and a second tapered conical portion 50 near the second axial end 35b of the collet.

As shown in FIGS. 2A, 3A and 3B, each of the drive elements 24, 32 includes respective conical surfaces 28, 36 which are adapted for abutting and sliding engagement with the tapered conical portions 48, 50 of the split collet 35. Flats 27, 37 on the respective drive elements 24, 32 (shown in FIGS. 3A and 3B) also meet in abutting engagement at the periphery of either axial end of the collet 35. As shown in FIGS. 2A and 3A, the first drive element 24 is initially spaced axially from the second drive element 32 and can be axially advanced toward the second drive element 32 by application of a clockwise rotational force to the first driver element 30 of the first drive element 24 with a rotatable driver 22. As shown in FIG. 3B, the conical surface 28 of the drive element 24 abuts the conical surface 48 of the collet 35, thereby driving the collet axially toward the second drive element 32. Further advancement of the first drive element 24 toward the collet 35 and the second drive element 32 causes conical surface 50 of the collet 35 to abut with conical surface 36 of the second drive element 32. In one form of the invention, the advancement of the first drive element 24 toward the second drive element 32 causes a radial compression of the collet 35 between them. The gap g in the circumference of the collet thus becomes relatively small, thereby decreasing the effective diameter of the collet and enabling it to grip an object, such as a cylindrical bone plug or an end of a ligament band.

As shown in FIG. 3B, the first and second drive elements engage to form a unitary structure with the collet 35 between them. The first drive element 24 can be axially retracted from the collet 35 and the second drive element 32 by application of a counterclockwise rotational force to the first driver element 30 of the first drive element 24. Disengagement of the first drive element 24 from the collet 35 opens the gap g in the collet and permits the collet to expand radially. The effective diameter of the collet 35 is thus increased to permit loosening of the bone plug or ligament band within the collet.

The radially compressible split collet 35 preferably has a textured interior surface 40 which can engage with a graft 44 in a frictional engagement. In one embodiment, the interior surface 40 includes a plurality of circumferentially extending ridges 52. The ridges 52 can have, for example, a sawtooth or helical tooth profile which extends radially toward the central axis 14, as shown in FIGS. 3A and 3B. In a preferred embodiment, the ridges have an asymmetrical profile with bearing surfaces 52a being transverse to axis 14, as shown most clearly in FIGS. 3A and 3B. The bearing surfaces are horizontal. In one form of the invention, the bearing surfaces 52a effectively form an internal thread pattern on the interior surface of the collet 35 which increases the holding strength of the collet by resisting axial forces which tend to dislodge the graft from the collet.

Figure 4E:
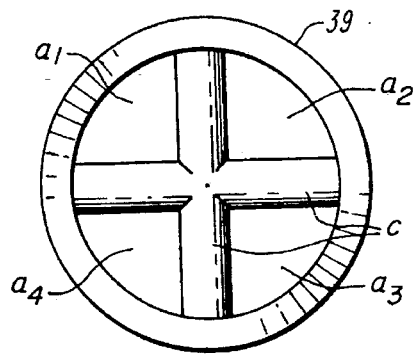
FIG. 4E is a plan view of a graft securing element according to still another embodiment of the invention.
Figure 4F:
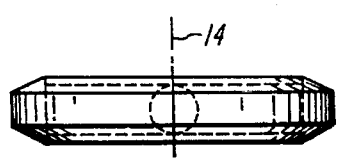
FIG. 4F is a side elevational view of the graft securing element of FIG. 4E.

FIGS. 2B, 4C, 4D, 4E and 4F illustrate other embodiments of the graft securing element 38. A flat disk fastener 39 includes a plurality of apertures $a_1$, $a_2$ for receiving a portion of a fibrous graft segment. The apertures are separated from one another by one or more transverse members c. The disk fastener 39 thus acts as a button or similar retaining device through which loops or segments of the graft, such as an ITB graft, can be passed and secured as shown in FIG. 8B. FIGS. 4E and 4F illustrate a preferred embodiment of the disk fastener 39 in which transverse members c form four distinct apertures $a_1$, $a_2$, $a_3$, $a_4$ for receiving one or more loops or segments of the graft. As shown in FIG. 8B, passage of the graft segments through diagonally opposing apertures $a_1$, $a_3$ or $a_2$, $a_4$ ensures that the segments remain substantially centrally located relative to the periphery of the disk 39 and relative to the bony channel 54. Other disk constructions and aperture configurations which achieve the desired results can also be used.

The graft fixation device 10 is preferably made of components which are durable and biocompatible with living tissue, such as for example, titanium. The exterior lateral surface 18 of the collar 12 and other bone-contacting surfaces of the device should be textured or otherwise finished to induce bone ingrowth into the device, thereby enhancing the biocompatibility and effectiveness of the device. Other inert and/or biocompatible materials and finishes known in the art can also be used.

Figure 5:
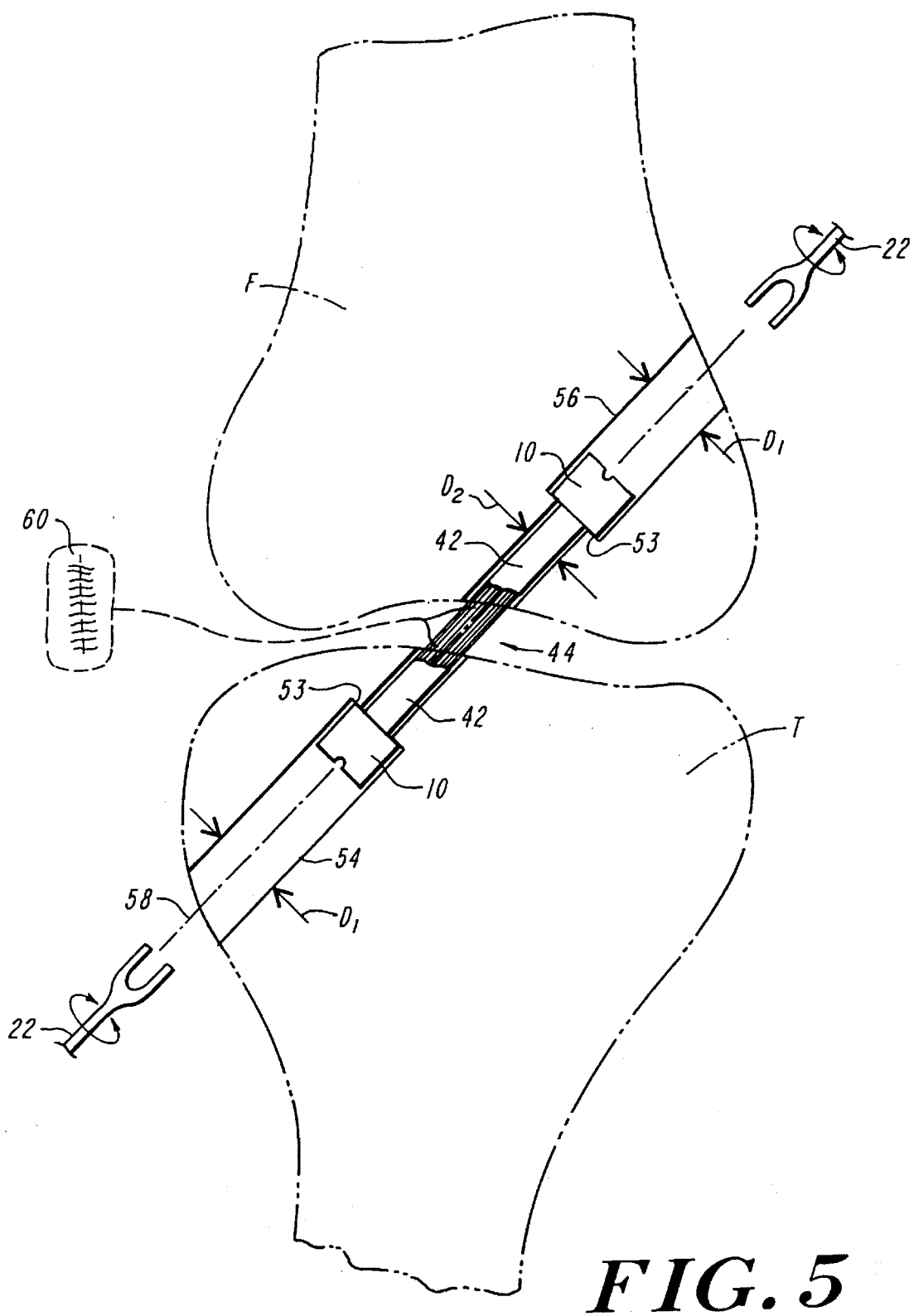
FIG. 5 is a simplified cutaway view of a BPTB graft in a graft fixation device implanted in a human knee joint according to one method of the invention.
Figure 6:
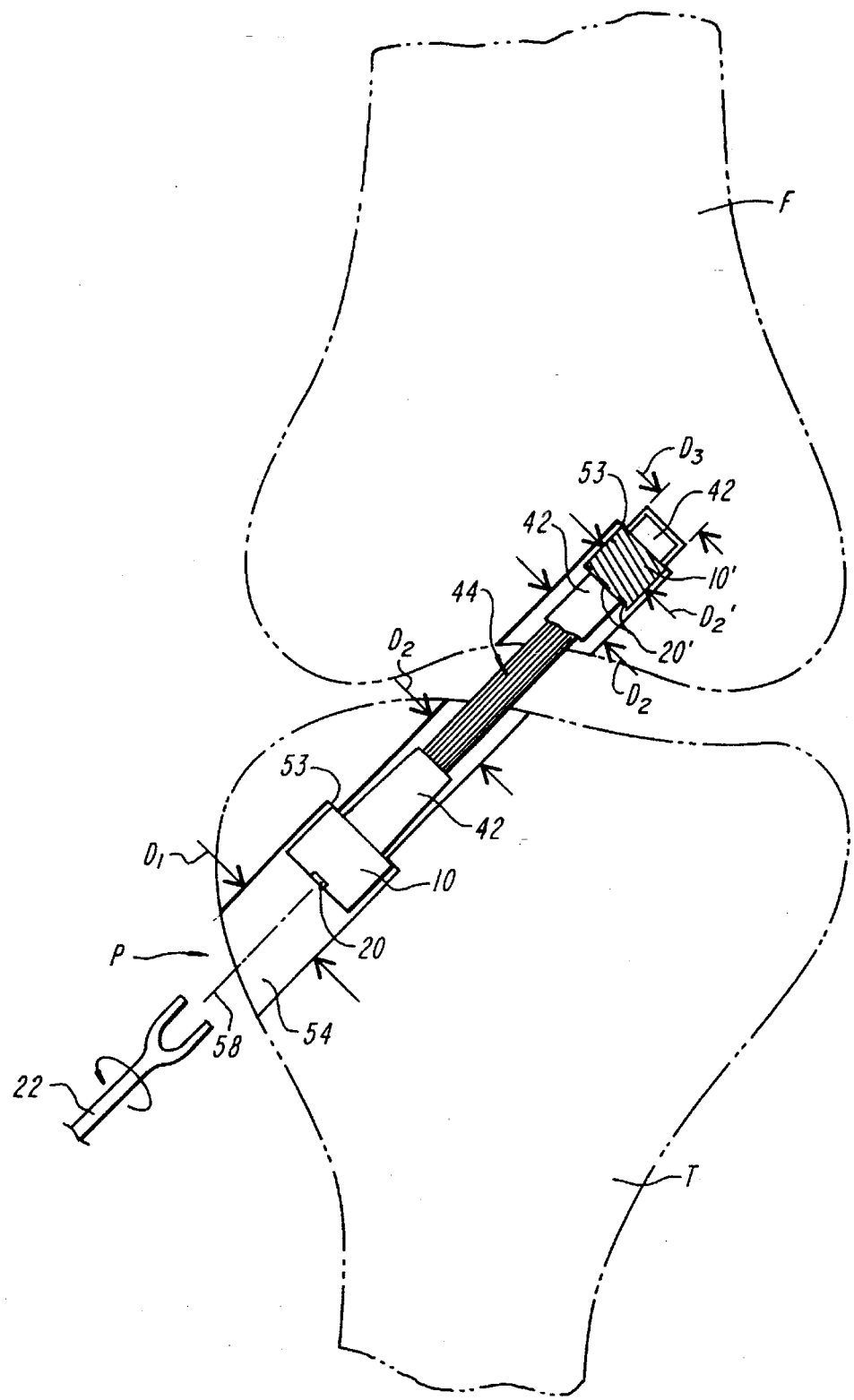
FIG. 6 is a simplified cutaway view of a BPTB graft in a graft fixation device implanted in a human knee joint according to another method of the invention.
Figure 7:
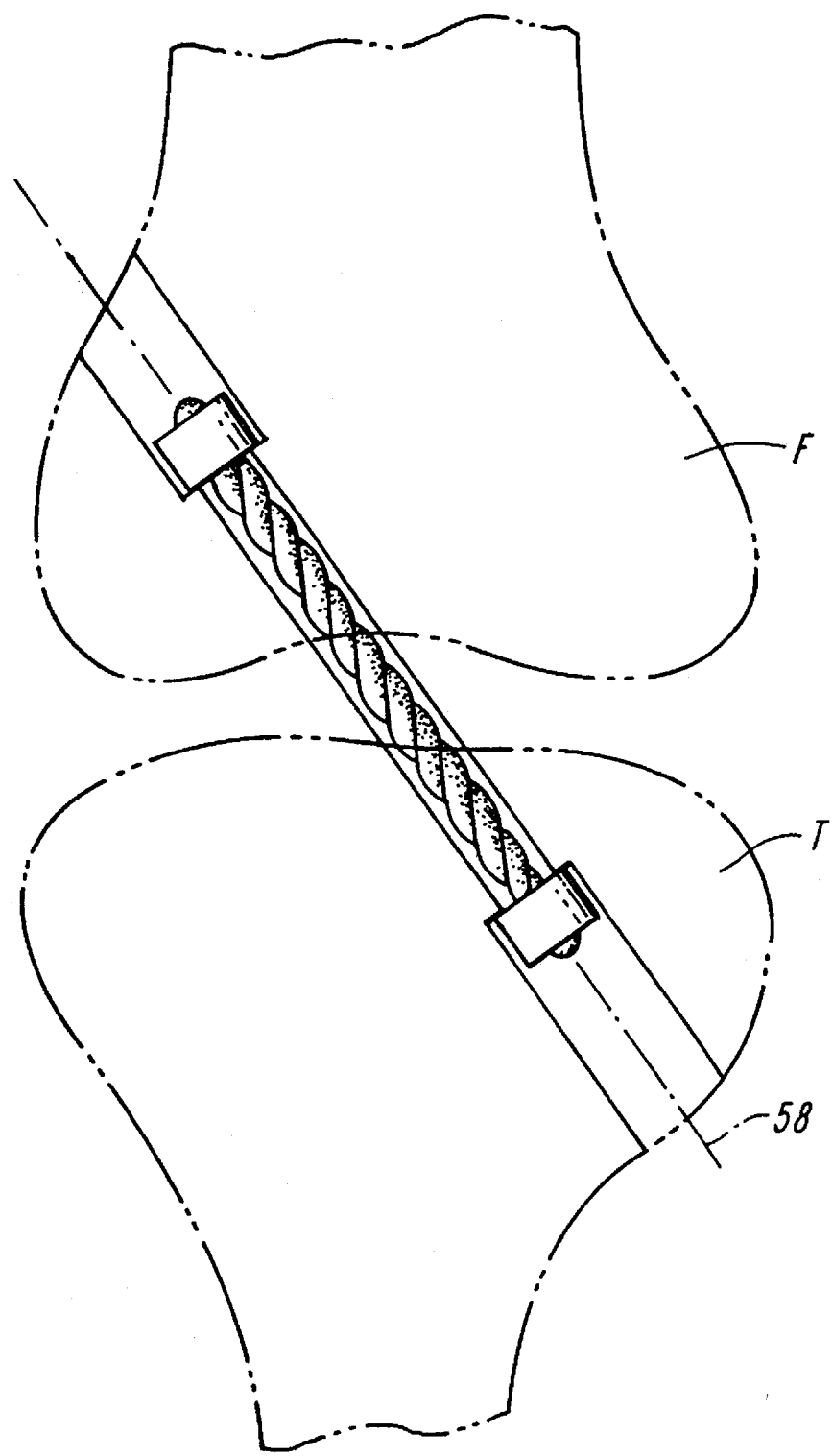
FIG. 7 is a simplified cutaway view of an ITB graft in a graft fixation device implanted in a human knee joint according to another method of the invention.

As shown most clearly in FIGS. 5–7, the graft fixation device 10 of the present invention is useful, for example, in reconstructive ACL surgery, in which a BPTB or ITB graft is inserted and fixed within a human knee joint (shown in phantom). The graft fixation device described herein can be made in a variety of inner and outer diameters to accommodate a wide variety of bony channel diameters and tissue graft/bone plug diameters.

According to one method of the invention, as shown in FIG. 5, bony channels 54 are drilled in a tibia T and a femur F according to anatomic guides for correct placement of the ACL substitute. The bony channels 54 can be drilled from two opposing locations, as shown in FIGS. 5 and 7, or from a single location to form a blind channel, as shown in FIG. 6 and explained more fully below. As shown in FIGS. 5–7, adjacent portions of the bony channels 54 having different diameters form a lip 53 against which the fixation device 10 abuts during placement of the device in the channel. The graft 44 is placed within the bony channels in preparation for fixation therein. A graft fixation device 10 is placed on the bony or fibrous segments 42 of the graft 44 so that the central axis 14 of the device 10 is substantially colinear with the axis 58 of the bony channel 54. The channel walls 56 preferably contact at least a portion of the bony or fibrous segments 42 of the graft and also portions of the exterior lateral surfaces 18 of the collar 12. The first and second drive elements 24, 32 are initially axially separated from one another so that the graft securing element 38, which can be a collet 35 or disk fastener 39, permits axial movement of the graft segment 42 therethrough. A rotatable driver 22 is then applied to the first driver element 30 to rotate the first drive element 24 relative to the collar 12, thereby advancing the drive element 24 axially toward the graft securing element 38 and the second drive element 32. The drive element 24 is axially advanced in this manner to sandwich the graft securing element 38 between the first and second drive elements 24, 32. As a result, a unitary structure comprising the first drive element 24, the graft securing element 38, and the second drive element 32 is formed which has a continuous external thread pattern on its exterior lateral surface which engages with the interior lateral threaded surface 16 of the collar 12.

In the embodiment in which the graft securing element 38 is a radially compressible split collet 35, radial compression of the collet 35 results from abutting engagement of the conical surface 28 of the first drive element 24 with the first tapered conical surface 48 of the collet 38, and abutting engagement of the conical surface 36 of the second drive element 32 with the second tapered conical surface 50 of the collet. The circumferential gap g of the collet becomes relatively small and the interior surface 40 of the collet engages frictionally with the bony or fibrous segment 42 of the graft, thereby axially fixing the graft segment within the collet 35 between drive elements 24, 32.

In the embodiment in which the graft securing element 38 is a disk fastener 39, axial advancement of the first drive element 24 against the disk fastener 39 and the second drive element 32 forms a unitary structure, thereby axially fixing the graft segment within the drive elements 24, 32 and disk fastener 39.

According to another aspect of the invention shown in FIG. 6, there is provided a method for anchoring a graft to an interior wall of a blind bone channel 54 drilled from a single entry portal P in the tibia T, and using two fixation devices 10' and 10. Fixation device 10 is substantially the same as device 10 in FIG. 5. Device 10' is similar but has a threaded outer surface as described below. The elements of device 10' which corresponds to similar elements in device 10 are noted below with the same, but primed, reference designations.

For use of the embodiment of FIG. 6, the bony channel 54 has several different diameters about a common axis 58, so that both the bony or fibrous portions 42 at both ends of the graft and the fixation devices 10 and 10' fit snugly in the respective portions of the bony channel 54. This similarity in size between the diameters of the channel, the graft and the graft fixation device provides up to 360 degrees of direct contact between the bony channel and the fixation device, and frequently between the bony channel and a portion of the graft, as shown in FIG. 6, thereby promoting rapid tissue ingrowth into both the graft and the graft fixation device.

The method comprises the steps of establishing a channel in a bone, the channel having a first proximal tibial portion having a diameter $D_1$, a second tibial portion distal to the first portion and having a diameter $D_2$, wherein $D_2<D_1$, a first femoral portion distal to the second tibial portion and having a diameter $D_2$, and a second femoral portion distal to the first femoral portion and having a diameter $D_3$, wherein $D_3<D_2$.

Figure 9:
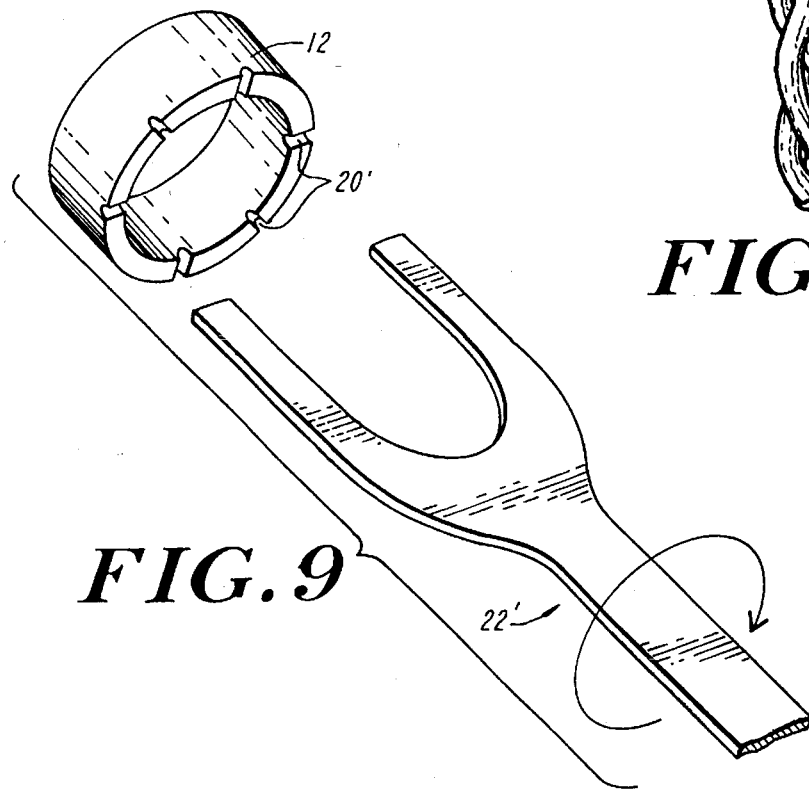
FIG. 9 is a side elevational view of a flexible shaft driver for use with the graft fixation device of the present invention.

The graft fixation device 10' is substantially as described above but having a threaded outer surface, with an, which has an outer diameter $D_2'$ such that $D_2'<D_2$ is positioned within the first femoral portion of the channel whereby the central axis 14 and the channel axis 58 are substantially colinear and the collar 12 is fixedly positioned with respect to the channel wall. A first bone plug portion 42 or ITB segment 19 of the graft is then positioned within the graft securing element 38 such that at least a portion of the first graft segment extends into a distal femoral portion of said channel having diameter $D_3$ where $D_3<D_2$. A flexible shaft spanner wrench 22', such as shown in FIG. 9, is then applied (via an auxiliary, angularly offset channel (not shown) which extends from the tibia surface and joins channel 54 beyond lip 53) to the first driver element 20' of device 10', and rotated to rotate the first drive element 24' relative to the collar 12 to axially advance the first drive element 24' toward the second drive element 32'. The first drive element 24 preferably includes a plurality of driver slots (not shown in FIG. 6) to facilitate engagement with the flexible shaft wrench 22', which can rotate through only a limited angle because of interference from the graft itself in the channel. The first and second drive elements 24', 32' engage the graft securing element 38' between them so that the first graft segment is axially fixed with respect to the drive elements. The flexible shaft spanner wrench 22' is then applied to the collar driver element 20' to rotate the collar within the first femoral of the channel to establish threads in the channel wall, thereby anchoring the collar therein. The collar also preferably has a plurality of driver slots 20' (shown in FIG. 9) to facilitate engagement with the flexible shaft wrench.

The method can further include the steps of providing a second graft fixation device 10' and fixing a second portion of the graft therein. The second graft fixation device is similar to the device 10 in FIG. 5, and can be substantially identical to the first graft fixation device 10' except that only the interior lateral surface of the collar is threaded. The respective drive elements 24, 32 of device 10 are adapted for receiving a rotatable driver 22 (which can be a cannulated, driver).

The second graft fixation device 10 has an outer diameter $D_1$ and is positioned within the first tibial portion of the channel so that the central axis 14 and the channel axis 58 are substantially colinear and the collar 12 is fixedly positioned with respect to the channel wall. A second segment of the graft is positioned within the graft securing 38 element such that at least a portion of the second graft segment extends into the second tibial portion of the channel. A rotatable driver 22 is applied to the first driver element 20 of the second fixation device 10 to rotate the first drive element 24 relative to the collar. The first drive element 24 axially advances toward the second drive element 32 to engage the graft securing element 38 between them, thereby fixing the second graft segment axially with respect to the drive elements.

The graft fixation device 10 can also be used to apply a desired axial tension and/or spiral twist to the graft 44 after the graft is fixed within the bony channels. For axial tension, rotational force from a driver 22 can be applied to the collar driver element 20 at the first end 12a of the collar 12 to move the collar axially relative to the drive elements 24, 32 and the graft securing element 38 between them. The threaded engagement of the outer lateral surfaces 26, 34 of the respective first and second drive elements 24, 32 with the interior surface 16 of the collar 12 permits axial movement of the drive elements 24, 32 relative to the collar 12. The graft 44 can thus be axially positioned within the channel 54 by rotating the collar 12 relative to the graft, which is fixed in the graft securing element 38 between the drive elements 24, 32. Angular twist can be imparted to the graft 44 by applying an axially advancing, or clockwise, rotational force to the first drive element 24 with a rotatable driver 22. The drive elements 24, 32 and graft securing element 38 engage and advance axially thereafter as a unit relative to the collar 12, which is fixed in the channel by means of abutment with lip 53. The unitary structure of drive elements 24, 32 and graft securing element 38 can thus be rotated about the central axis 14 and channel axis 58, which are substantially colinear, to a desired angular orientation with respect to those axes.

In one embodiment, the diameter $D_3$ of the second femoral portion of the bony channel is selected to substantially match the diameter of the first segment of the graft, and the diameter $D_2$ of the second tibial portion and first femoral portion of the bony channel is selected to substantially match the diameter of the second segment of the graft, as shown in FIG. 6.

A strain gauge device 60, shown in phantom in FIG. 5, can be coupled to the graft 44 in situ for measuring tension in the graft 44 during movement of the surrounding joint through a range of motion.

The novel construction of the device 10 ensures fixation of the bony or fibrous segments 42 of a graft 44 within a bony channel 54, and permits independent axial and angular movement of the graft 44 without dislodging the graft from the channels 54 or from the fixation device 10.

Figure 8A:
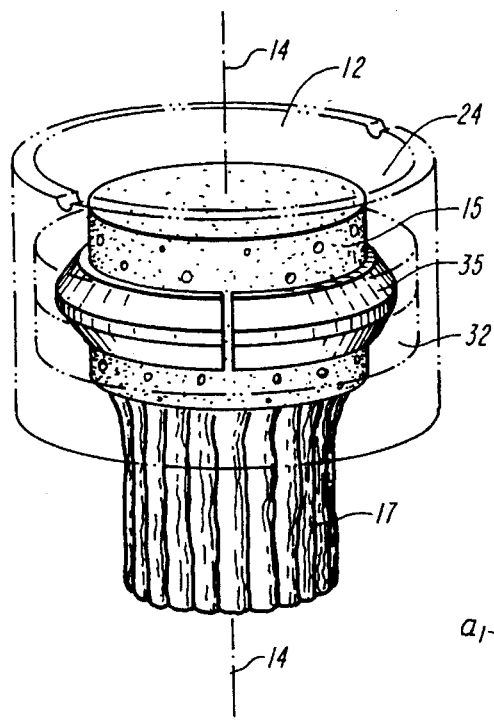
FIG. 8A is a perspective view of a BPTB graft fixed in the graft fixation device of FIG. 2A.
Figure 8B:
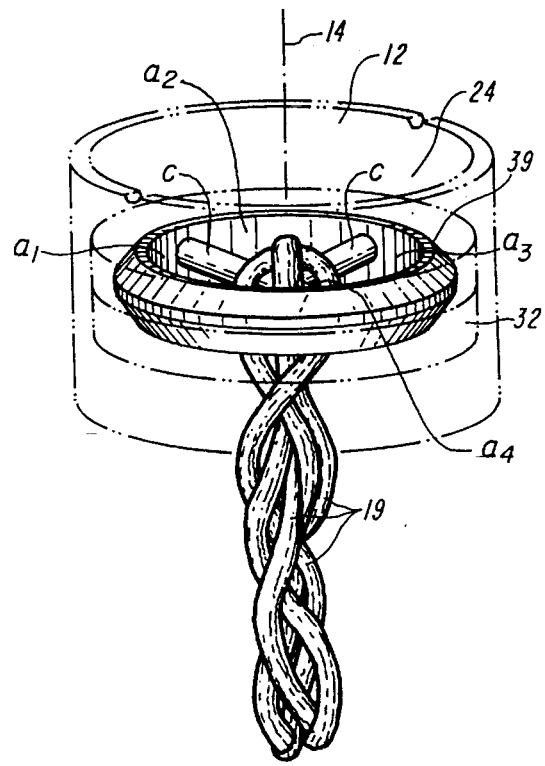
FIG. 8B is a perspective view of an ITB graft fixed in the graft fixation device of FIG. 2B.

FIGS. 8A and 8B illustrate, respectively, the fixation of a BPTB graft and an ITB graft within the graft fixation devices of the present invention. In FIG. 8A, a bone plug 15 of a BPTB graft is secured in a radially compressible split collet 35, which is held in compression between drive elements 24 and 32 in collar 12 (shown in phantom). Ligament portion 17 extends into the bone channel along axis 14. In FIG. 8B, a plurality of ligament bands 19 of an ITB graft are looped over transverse members c of a disk fastener 39, which is held compressively between drive elements 24 and 32 within collar 12 (shown in phantom).

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description. All changes that come within the meaning and range of the equivalency of the claims are therefore intended to be embraced therein.

What is claimed is:

1. A graft fixation device, comprising:
    A. an annular collar disposed about and extending along a central axis, said collar having a first end, a second end, an interior lateral surface, and an exterior lateral surface, said interior lateral surface being threaded about and along said central axis, said collar further having at said first end collar driver means for receiving an external driver rotatable about said central axis,
    B. a first annular drive element disposed concentrically within said collar and having a first end closest to said first end of said collar and a second end opposite thereto, and further having:
        i. an outer lateral surface in threaded engagement with said threaded interior surface of said collar,
        ii. an inner lateral surface disposed about said central axis,
        iii. first driver means at said first end of said drive element for receiving an external driver rotatable about said central axis,
    C. a second annular drive element disposed concentrically within said collar and having a first end closest to said second end of said collar and a second end opposite thereto, and further having:
        i. an outer lateral surface in threaded engagement with said threaded interior surface of said collar,
        ii. an inner lateral surface disposed about said central axis, and
    D. tissue securing means disposed concentrically within said collar between said first and second drive elements for releasably securing at least a portion of said graft.

2. A graft fixation device according to claim 1, wherein said first annular drive element has a conical inner lateral surface having a first radius proximate said first end of said drive element and a second, larger radius proximate near said second end of said drive element, and wherein said second annular drive element has a conical inner lateral surface having a first radius proximate said first end of said drive element and a second larger radius said second end of said drive element, and wherein said tissue securing means comprises a radially compressible split collet extending circumferentially between two circumferential ends separated by a gap, and having
    i. a first axial end closest to said first drive element,
    ii. a second axial end closest to said second drive element,
    iii. an interior surface, said interior surface being adapted for frictional engagement with an object interior thereto, and
    iv. an outer lateral surface having a first tapered conical portion proximate said first axial end of said collet and a second tapered conical portion proximate said second axial end of said collet.

3. A graft fixation device according to claim 2, wherein said interior surface of said collet includes a plurality of circumferentially extending ridges.

4. A graft fixation device according to claim 3, wherein said ridges have a sawtooth profile extending in the direction of said central axis.

5. A graft fixation device according to claim 4, wherein the surfaces of said ridges are transverse to said central axis.

6. A graft fixation device according to claim 5, wherein said ridges have horizontal surfaces.

7. A graft fixation device according to claim 3, wherein said ridges have a helical profile about said central axis.

8. A graft fixation device according to claim 1, wherein said exterior lateral surface of said collar is threaded.

9. A graft fixation device according to claim 1, wherein said tissue securing means comprises a disk having a plurality of apertures for receiving at least a portion of a graft segment therethrough.

* * * * *